(12) United States Patent
Millerd (10) Patent No.: US 7,198,617 B2
(45) Date of Patent: Apr. 3, 2007

(54) PASSIVELY GUARDED, FILLABLE INJECTION SYRINGE

(75) Inventor: Don Millerd, San Diego, CA (US)

(73) Assignee: Visual Connection, Inc., San Deigo, CA (US)

( * ) Notice: Subject to any disclaimer, the term of this patent is extended or adjusted under 35 U.S.C. 154(b) by 33 days.

(21) Appl. No.: 10/983,108

(22) Filed: Nov. 5, 2004

(65) Prior Publication Data

US 2006/0111675 A1  May 25, 2006

(51) Int. Cl.
*A61M 5/32* (2006.01)
(52) U.S. Cl. .................. 604/192; 604/110; 604/187; 604/198; 604/506; 604/500
(58) Field of Classification Search ............... 604/187, 604/110, 192, 506, 198, 135, 500
See application file for complete search history.

(56) References Cited

U.S. PATENT DOCUMENTS

| | | | |
|---|---|---|---|
| 2,679,246 A * | 5/1954 | Cohen ..................... 604/231 |
| 4,425,120 A | 1/1984 | Sampson et al. |
| 4,664,654 A | 5/1987 | Strauss |
| 4,681,567 A | 7/1987 | Masters et al. |
| 4,781,692 A | 11/1988 | Jagger et al. |
| 4,894,055 A | 1/1990 | Sudnak |
| 4,911,693 A | 3/1990 | Paris |
| 5,037,402 A | 8/1991 | Bartman |
| 5,061,251 A | 10/1991 | Juhasz |
| 5,104,384 A | 4/1992 | Parry |
| 5,167,635 A | 12/1992 | Haber et al. |
| 5,167,640 A | 12/1992 | Balding |
| 5,176,656 A | 1/1993 | Bayless |
| 5,197,953 A | 3/1993 | Colonna |
| 5,222,945 A | 6/1993 | Basnight |
| 5,232,457 A | 8/1993 | Grim |
| 5,242,420 A | 9/1993 | Martin |
| 5,267,972 A | 12/1993 | Anderson |
| 5,267,977 A | 12/1993 | Feeney, Jr. |
| 5,279,566 A | 1/1994 | Kline, Jr. et al. |
| 5,292,314 A | 3/1994 | D'Alessio et al. |
| 5,295,975 A | 3/1994 | Lockwood, Jr. |
| 5,300,040 A | 4/1994 | Martin |
| 5,324,265 A | 6/1994 | Murray et al. |
| 5,346,480 A | 9/1994 | Hess et al. |
| 5,376,080 A | 12/1994 | Petrussa |
| 5,389,085 A | 2/1995 | D'Alessio et al. |

(Continued)

*Primary Examiner*—Kevin C. Sirmons
*Assistant Examiner*—Phillip Gray
(74) *Attorney, Agent, or Firm*—Nydegger & Associates (57) ABSTRACT

A passively guarded, fillable injection syringe includes an adapter for holding the proximal end of a hollow needle. An inverted plunger is slidingly mounted on the adapter to establish a medicament chamber that is in fluid communication with the needle. Also, a substantially cylindrical needle guard is positioned on the needle for reciprocal axial movement under the influence of a spring which biases the guard and adapter in opposite axial directions. A mechanism is provided such that plunger movements that are required in a typical fill and inject procedure also function to control the position of the guard relative to the needle. Initially, the guard is locked covering the needle tip. A plunger movement unlocks the guard and retracts the guard for syringe filling and injection. Depressing the plunger to complete the injection releases the guard for distal movement under the spring force into a needle protecting position.

20 Claims, 5 Drawing Sheets

U.S. PATENT DOCUMENTS

| | | |
|---|---|---|
| 5,403,286 A | 4/1995 | Lockwood, Jr. |
| 5,478,316 A * | 12/1995 | Bitdinger et al. ............ 604/135 |
| 5,540,667 A | 7/1996 | Tanner, II |
| 5,582,597 A | 12/1996 | Brimhall et al. |
| 5,591,138 A | 1/1997 | Vaillancourt |
| 5,681,292 A * | 10/1997 | Tober et al. ................. 604/195 |
| 5,695,475 A | 12/1997 | Best, Jr. et al. |
| 6,162,197 A | 12/2000 | Mohammad |
| 6,379,336 B1 | 4/2002 | Asbaghi et al. |
| 6,530,905 B2 | 3/2003 | Asbaghi |
| 6,626,864 B2 * | 9/2003 | Jansen et al. ................ 604/110 |
| 2003/0212380 A1 * | 11/2003 | Barrelle ....................... 604/506 |

* cited by examiner

PASSIVELY GUARDED, FILLABLE INJECTION SYRINGE

FIELD OF THE INVENTION

The present invention pertains generally to syringes for medical use. More particularly, the present invention pertains to protective devices for injection syringes that are filled by the user prior to the administration of an injection. The present invention is particularly, but not exclusively, useful for passively covering and protecting the needle of an injection syringe after its use.

BACKGROUND OF THE INVENTION

Recent research from the Centers for Disease Control and Prevention (CDC) shows that approximately 384,000 needle sticks or similar injuries occur among health care workers in U.S. hospitals each year. Unfortunately, each accidental needle stick has the potential to expose a health care worker to a life-threatening virus such as hepatitis or HIV. In addition to the needle sticks that occur in hospitals, accidental needle sticks can also occur in other health care settings. For example, needle stick injuries can occur at clinics or during home health care. In fact, some studies have estimated that over 600,000 needle sticks occur in the U.S. each year, and approximately 1,000 of these accidental needle sticks result in a life-threatening infection.

For each accidental needle stick, health care providers are obligated to test and counsel the exposed worker. Further, follow-up testing for HIV must be conducted approximately six months after the exposure. It is to be appreciated that the costs associated with the testing, lab work, the worker's lost time, and the associated tracking and administrative costs, can be considerable.

Accidental needle sticks can occur in several ways. For example, sudden movement by the patient can cause a health care worker to lose control of a syringe, resulting in injury. Attempts to manually recap a needle following an injection can also result in injury. Moreover, injuries often result when contaminated, unprotected needles are left unattended or disposed of improperly. In addition to accidental needle sticks, unnecessary exposure to bloodborne pathogens can result when a health care worker mistakenly reuses a contaminated needle on a patient.

One particular type of syringe that is prone to needle stick injuries is the fillable injection syringe. In overview, these fillable injection syringes are designed to be filled with a medicament from a medicament vial by the same user that administers an injection. Heretofore, a typical procedure has involved removing a cap that covers the sharp needle tip of the fillable injection syringe. With the needle exposed, the needle tip is inserted into a vial containing medicament. This step generally occurs just prior to an injection. Next, the plunger is depressed to void the syringe chamber of air. With the syringe voided, the plunger is retracted to draw a specified quantity of medicament into the syringe chamber. Once the medicament has been loaded into the syringe, the needle is then inserted into a patient and the plunger is depressed to inject the medicament into the patient. After the injection, the needle is removed from the patient and often must be manually recapped to protect the contaminated needle. After recapping, it is often difficult to distinguish between used and unused syringes.

In light of the above, it is an object of the present invention to provide a fillable medical syringe that passively covers and protects the needle of the syringe after first filling the syringe with medicament and then injecting the medicament into a patient. It is another object of the present invention to provide a fillable syringe which guards the needle prior to an injection procedure and uses the same guard to passively guard the needle after an injection procedure. It is still another object of the present invention to provide a passively guarded, fillable injection syringe in which the position of the needle guard is controlled and regulated by plunger movements that are required in a typical fill and inject procedure.

It is yet another object of the present invention to provide a fillable injection syringe having an integral mechanism that prevents reuse of the syringe (after use and contamination) by disabling the plunger at the completion of an injection procedure. Yet another object of the present invention is to provide a protective device for a medical syringe that is easy to use, relatively simple to implement, and comparatively cost effective.

SUMMARY OF THE INVENTION

A passively guarded, fillable injection syringe includes an elongated hollow needle that defines an axis and has a sharp, distal needle tip. The syringe also includes an adapter for holding the proximal end of the needle. With this cooperation of structure, the needle extends in a distal direction from the adapter. In addition, an inverted plunger is slidingly mounted on the adapter to establish a medicament chamber that is in fluid communication with the needle. For the present invention, a substantially cylindrical needle guard is positioned on the needle for reciprocal axial movement relative to the needle. Also, a spring is positioned between the guard and the adapter to bias the guard along the axis in a distal direction away from the adapter.

As described in greater detail below, a mechanism is provided to selectively engage and disengage the plunger and guard during the course of an injection procedure. More specifically, the plunger movements that are required to fill the syringe and dispense a medicament from the syringe also function to control the position of the guard relative to the needle. In functional overview, prior to an injection procedure, the guard is locked in a distal position covering the tip of the needle and can only be unlocked by a movement of the plunger. Once unlocked, the guard can be retracted to expose the needle tip. This allows the needle tip to be inserted into a medicament vial to fill the syringe, and in addition, allows the exposed needle to be inserted into a patient for an injection. When the plunger is withdrawn proximally relative to the adapter, the plunger and guard engage and the guard moves proximally to expose the needle. On the other hand, when the plunger is depressed (i.e. moved distally), the plunger releases the guard. Once released, the guard is free to move distally under the influence of the spring. As a consequence of this interaction, after the plunger is depressed to complete an injection, the guard is released and allowed to translate distally, relative to the needle, to cover and protect the needle tip.

In greater structural detail, the adapter includes a substantially cylindrical portion that is centered on the needle axis and has a proximal end and an open distal end. In addition, a standoff is formed at the proximal end of the adapter to attach the proximal end of the needle to the adapter. From the standoff, the needle passes distally through the cylindrical adapter and extends beyond the adapter's distal end to a distal needle tip. Also, the adapter is sized to allow the cylindrical guard to move axially along the needle and within the cylindrical portion of the adapter.

In a typical embodiment of the present invention, the syringe includes an inverted plunger that has a substantially cylindrical portion which extends from a closed proximal end to an open distal end. Structurally, the cylindrical portion surrounds a medicament chamber and is slidingly mounted on the proximal end of the adapter. A seal is interposed between the proximal end of the adapter and the cylindrical portion of the plunger to establish fluid communication between the medicament chamber and the lumen of the needle. With this arrangement, the plunger can be retracted to draw fluid through the needle and into the chamber and the plunger can be depressed to expel fluid from the chamber and out of the needle's distal tip.

As indicated above, a mechanism is provided to selectively engage and disengage the plunger and guard during the course of an injection procedure. Structurally, this mechanism includes a tang that is formed on the cylindrical portion of the plunger and an axially aligned slot that is formed in the guard. Specifically, the tang extends distally and inwardly toward the needle axis from the cylindrical portion of the plunger. An axially aligned slit formed in the adapter allows the tang to pass through the adapter and interact with the slot in the guard. In greater structural detail, the guard slot has a proximal end that is formed as an abutment and a distal end that is formed as a ramp. With this arrangement, the tang engages the abutment during a proximal movement of the plunger to engage the plunger with the guard. On the other hand, during a distal movement of the plunger, the ramp directs the tang out of the slot and disengages the guard and plunger.

In another aspect of the invention, the syringe includes a mechanism to lock the guard in a distal position covering the tip of the needle prior to an injection procedure. Specifically, once locked by the mechanism, the guard can only be unlocked by a movement of the plunger. For this purpose, the cylindrical adapter is formed with a cam lever having a distal lever end and a cam surface. For the syringe, the cam lever is deflectable by the cylindrical portion of the plunger from a relaxed position to a biased position. In the relaxed position, the cam surface extends radially outward from the remaining cylindrical section of the adapter. On the other hand, in the biased position, the lever end extends radially inward from the remaining cylindrical section of the adapter. When the plunger is in a distal position, the cylindrical portion of the plunger contacts the cam surface and deflects the cam lever into the biased position. Functionally when the cam lever is in the biased position, the lever end engages the guard and prevents a proximal movement of the guard. When the plunger is retracted, the cam lever relaxes and unlocks the guard.

In one particular embodiment of the invention, the syringe includes a substantially cylindrical shaped syringe body that is formed with open distal and proximal ends. A flange is formed at the distal end of the syringe body and extends radially inward relative to the cylindrical portion of the syringe body. At the proximal end, the syringe body is formed with a finger grip that extends radially outward form the cylindrical portion. For the syringe, the body is slidingly mounted on the adapter. Specifically, the syringe body is capable of an axial movement relative to the adapter from an operational position to a locking position. In the operational position, the syringe body does not interfere with relative movement between the guard and adapter. In the locking position, however, the flange at the distal end of the syringe body deflects the cam lever and holds the cam lever in the biased position (i.e. the position where the guard is locked). After an injection, the syringe body can be moved proximally relative to both the plunger and adapter and into the locking position. This then locks the guard into a needle tip covering position and prevents inadvertent reuse of the syringe.

Another safety feature that can be incorporated into the syringe includes a recess that is formed in the syringe body at the body's proximal end. Specifically, this recess is sized and positioned to receive a grip flange that is formed at the proximal end of the plunger. After an injection, the plunger can be advanced until the grip flange is positioned in the recess. With the grip flange positioned in the recess, subsequent movement of the plunger relative to the syringe body is effectively prevented.

In operation, the plunger is initially located in a distal position relative to the adapter with the tang extending into the slot. In this configuration, the cylindrical portion of the plunger holds the cam lever deflected inward into the biased position in which the guard is locked. Next, the plunger is withdrawn proximally. The effect of this proximal movement is threefold. First, initial proximal movement of the plunger allows the cam lever to relax and unlock the guard. Second, additional proximal movement engages the tang of the plunger with the proximal abutment in the slot, causing the guard to move proximally with the plunger. Third, proximal movement of the plunger draws air through the needle and into the medicament chamber.

With the guard retracted, the next step is to insert the exposed distal tip of the needle into a medicament vial. At this point, the plunger can be depressed to expel air into the vial and void the medicament chamber. During plunger advancement, the ramp formed at the distal end of the slot directs the tang out of the slot and disengages the guard from the plunger. Thus, distal guard movement is only prevented by the contact between the guard and the vial at this point. Next, the plunger can be withdrawn to fill the chamber with medicament. During this plunger withdrawal, the tang reenters the slot and engages the proximal abutment. The result is that the plunger engages the guard and prevents distal advancement of the guard relative to the needle. Thus, when the needle is removed from the vial, the distal tip of the needle remains unguarded and exposed. The syringe is now ready for an injection.

To inject a medicament into a patient, the distal tip of the needle is inserted into the patient and the plunger depressed. This distal advancement of the plunger releases the guard. Specifically, during plunger advancement, the ramp formed at the distal end of the slot directs the tang out of the slot and disengages the guard from the plunger. Once released, the guard is free to move distally under the influence of the spring. Thus, as the needle is withdrawn from the patient, the needle retracts proximally into the guard which remains in contact with the patient's skin. Once the syringe has been removed from the patient, the plunger and adapter can be advanced distally relative to the syringe body to lock the guard in place. This also places the grip flange of the plunger in the recess formed in the syringe body. Functionally, in this last configuration, the guard completely covers the hollow needle to protect the user from unwanted needle sticks and prevents inadvertent reuse of the syringe.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
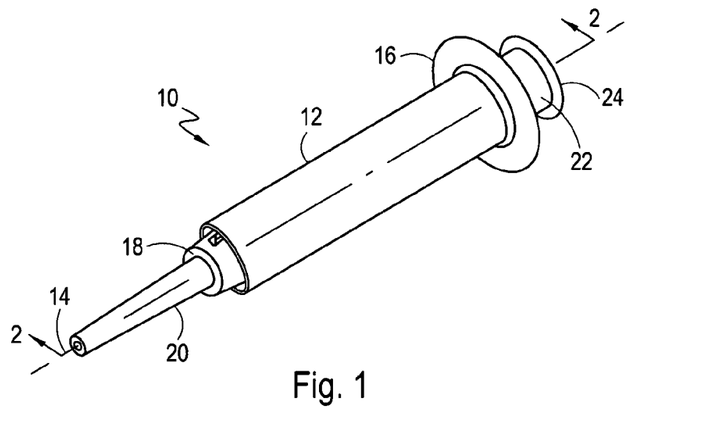
FIG. 1 is a perspective view of a passively guarded, fillable injection syringe, shown in its initial configuration.

Referring initially to FIG. 1, a passively guarded, fillable injection syringe is shown and generally designated 10. As shown in FIG. 1, the syringe 10 includes a substantially cylindrical syringe body 12 that is centered on a needle axis 14 and formed with a finger grip 16 at its proximal end. FIG. 1 further shows that the syringe 10 includes an adapter 18 that is sized to fit within the syringe body 12 and includes a cylindrical portion that is also centered on the needle axis 14. For the syringe 10, a substantially cylindrical needle guard 20 is provided that is positioned co-axially with both the syringe body 12 and adapter 18, and is sized to fit within the adapter 18. For the embodiment shown, the guard 20 is formed with a slight taper characterized by a decreasing outside diameter in a distal direction. It can be further seen that the syringe 10 includes a plunger 22 that is formed with a grip flange 24 at its proximal end.

Figure 2A:
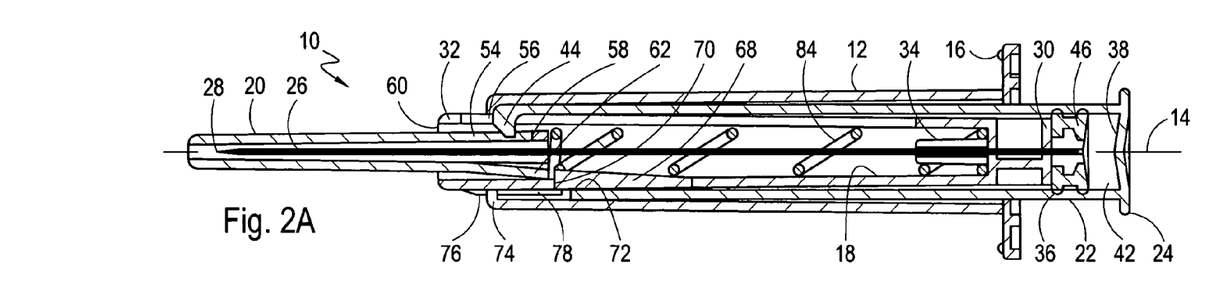
FIG. 2A is a sectional view of the syringe as seen along line 2—2 in FIG. 1, shown in its initial configuration in which the guard is locked over the needle's distal tip.

As best seen in FIG. 2A, the passively guarded, fillable injection syringe 10 includes a straight, elongated hollow needle 26 that has a sharp, distal needle tip 28. FIG. 2A also shows that the adapter 18 includes a substantially cylindrical portion that is centered on the needle axis 14 and has a proximal end 30 and an open distal end 32. A standoff 34 is formed at the proximal end 30 of the adapter 18 to attach the proximal end of the needle 26 to the adapter 18. As shown in FIG. 2A, from the standoff 34, the needle 26 passes distally through the cylindrical adapter 18 and extends beyond the adapter's open distal end 32 to the distal needle tip 28. As best seen in FIG. 2A, the adapter 18 is sized to allow the cylindrical guard 20 to move axially along the needle 26 and within the cylindrical portion of the adapter 18.

Figure 4:
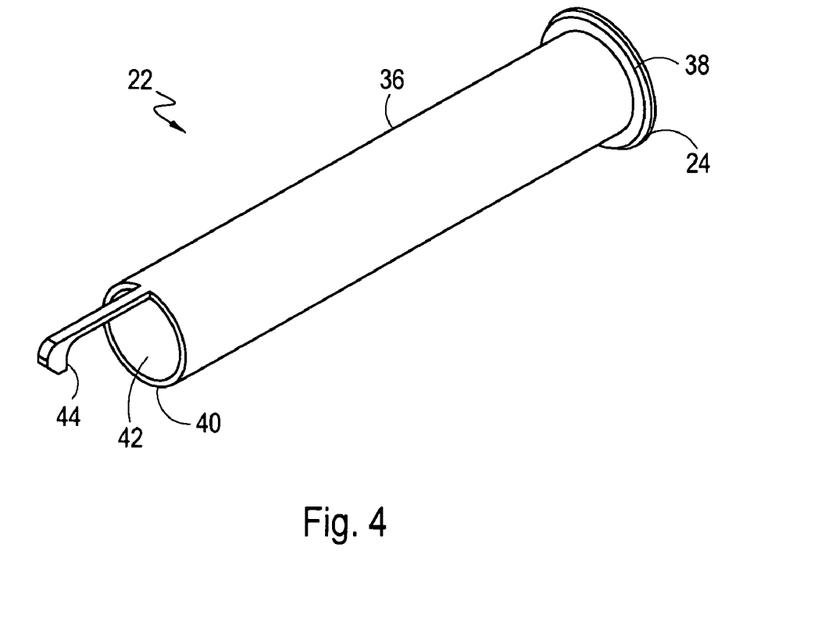
FIG. 4 is a perspective view of a plunger for use in the syringe shown in FIG. 1.

Cross-referencing FIGS. 2A and 4, it can be seen that the inverted plunger 22 has a substantially cylindrical portion 36 which extends from a closed proximal end 38 to an open distal end 40. Structurally, the cylindrical portion 36 surrounds a medicament chamber 42 and is slidingly mounted on the proximal end 30 of the adapter 18. FIGS. 2A and 4 further show that the plunger 22 is formed with a tang 44 that extends distally and inwardly (i.e. toward the needle axis 14) from the cylindrical portion 36 of the plunger 22.

Figure 5:
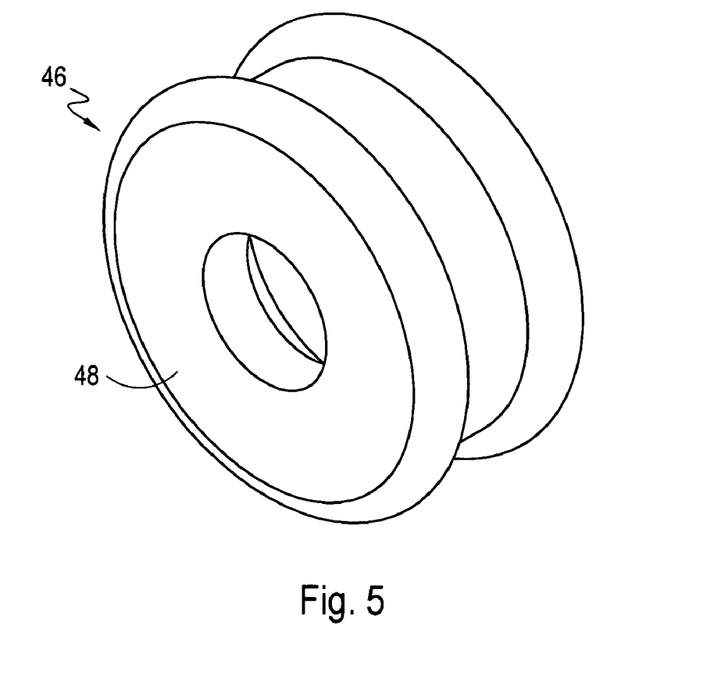
FIG. 5 is a perspective view of a seal for use in the syringe shown in FIG. 1.

Cross-referencing FIGS. 2A and 5, it can be seen that the syringe 10 includes an elastomeric seal 46 that is attached onto the proximal end 30 (best seen in FIG. 2A) of the adapter 18. As shown, the seal 46 has a generally fusiform shape or spindle-like shape and is formed with a through-hole 48. When the open distal end 40 of the plunger 22 is slid over the proximal end 30 of the adapter 18, the seal 46 compresses between the adapter 18 and the cylindrical portion 36 of the plunger 22 to establish sealed fluid communication between the medicament chamber 42 and the lumen of the needle 26. With this arrangement, the plunger 22 can be retracted to draw fluid through the needle 26 and into the chamber 42 and, in addition, the plunger 22 can be depressed to expel fluid from the chamber 42 and out of the needle's distal tip 28.

Figure 3A:
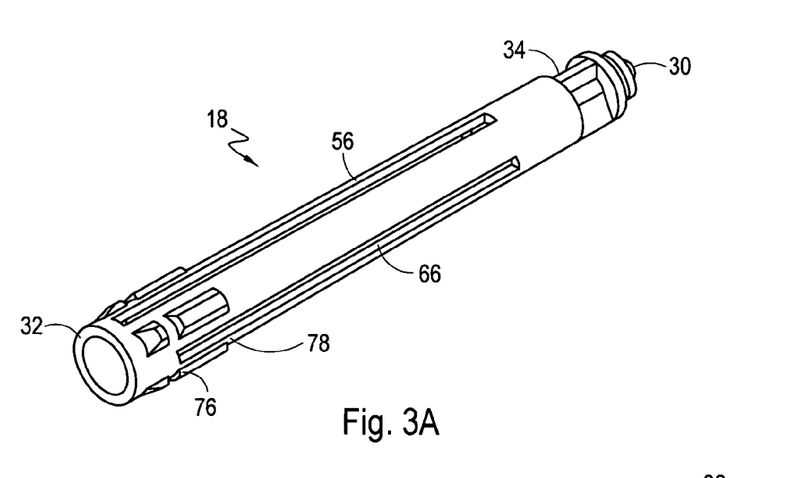
FIG. 3A is a top, front perspective view of an adapter for use in the syringe shown in FIG. 1.
Figure 6A:
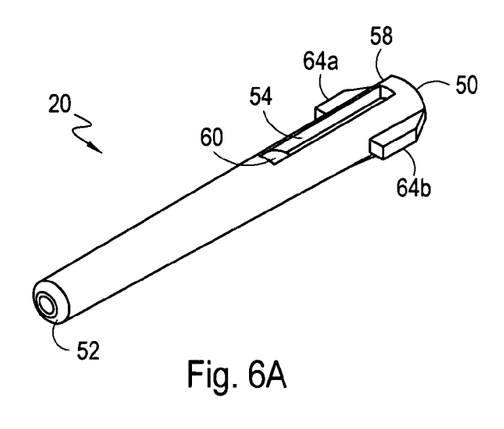
FIG. 6A is a top, front, perspective view of a guard for use in the syringe shown in FIG. 1.
Figure 6B:
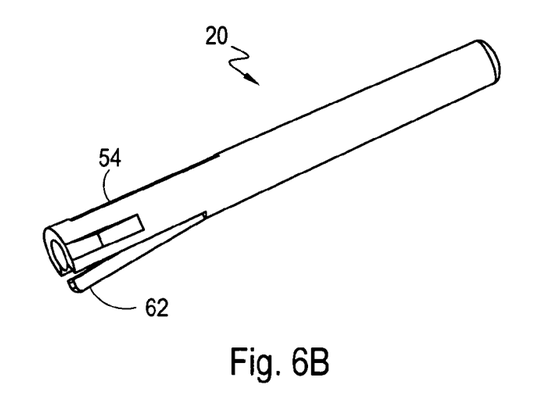
FIG. 6B is a bottom, rear perspective view of the guard shown in FIG. 6A.

The structure of the guard 20 can be best appreciated with initial reference to FIGS. 2A and 6A. As shown there, the guard 20 extends from an open proximal end 50 to an open distal end 52 and is formed with an axially aligned slot 54 for interaction with the tang 44. Specifically, as shown in FIGS. 2A and 3A, an axially aligned slit 56 formed in the adapter 18 allows the tang 44 to pass through the adapter 18 and interact with the slot 54 in the guard 20. As best seen with cross-reference to FIGS. 2A and 6A, the guard slot 54 has a proximal end that is formed as an abutment 58 and a distal end that is formed as a ramp 60. With this arrangement, the tang 44 engages the abutment 58 during a proximal movement of the plunger 22 to engage the plunger 22 with the guard 20. On the other hand, during a distal movement of the plunger 22, the ramp 60 directs the tang 44 out of the slot 54 and disengages the guard 20 and plunger 22. As seen in FIGS. 2A and 6B, the guard 20 is also formed with a living hinge 62 that extends radially outward when in a relaxed, undeflected state. FIG. 6A further shows that the guard 20 is formed with two alignment guides 64a,b which each extend radially outward from the cylindrical portion of the guard 20. These alignment guides 64a,b travel within a pair of corresponding slots 66 (see FIG. 3A) in the adapter 18 and maintain the guide 20 azimuthally aligned within the adapter 18.

Figure 2B:
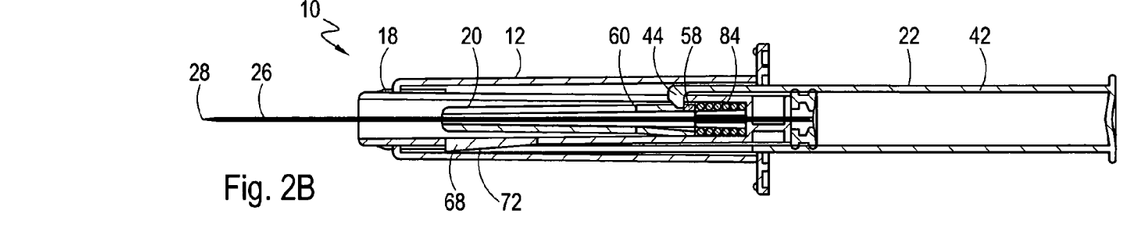
FIG. 2B is a sectional view of the syringe as in FIG. 2A, shown after a plunger movement has unlocked and distally retracted the guard.
Figure 3B:
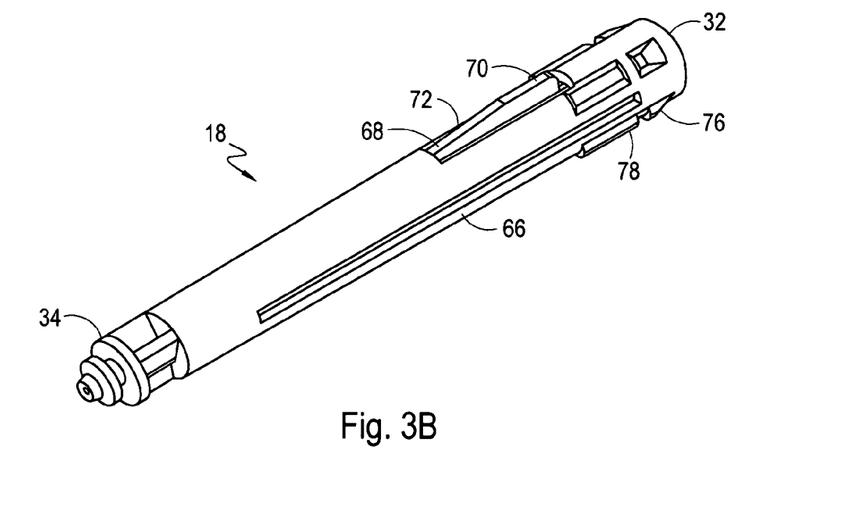
FIG. 3B is a bottom, rear perspective view of the adapter shown in FIG. 3A.

By cross-referencing FIG. 2A with FIG. 3B, it can be seen that the syringe 10 includes a mechanism to lock the guard 20 in a distal position covering the needle tip 28 prior to an injection procedure. Specifically, once locked by the mechanism, the guard 20 can only be unlocked by a movement of the plunger 22. Specifically, as shown, the cylindrical adapter 18 is formed with a cam lever 68 having a distal lever end 70 and a cam surface 72. Comparing FIG. 2A with FIG. 2B, it can be seen that the cam lever 68 is deflectable by the cylindrical portion 36 of the plunger 22 from a relaxed position (FIG. 2B) to a biased position (FIG. 2A). In the relaxed position (FIG. 2B), the cam surface 72 extends radially outward from the remaining cylindrical section of the adapter 18. On the other hand, as shown in FIG. 2A, in the biased (i.e. deflected) position, the lever end 70 extends radially inward from the remaining cylindrical section of the adapter 18. When the plunger 22 is in the distal position shown in FIG. 2A, the cylindrical portion 36 of the plunger 22 contacts the cam surface 72 and deflects the cam lever 68 into the biased position. Functionally, as shown in FIG. 2A, when the cam lever 68 is in the biased position, the lever end 70 engages the hinge 62 of the guard 20 and prevents a proximal movement of the guard 20 relative to the needle 26. When the plunger 22 is retracted as shown in FIG. 2B, the cam lever 68 relaxes into its undeflected, outward position (as shown in FIG. 3B) and allows the guard 20 to move distally relative to the needle 26.

FIG. 2A shows that the distal end of the cylindrical syringe body 12 is formed with a flange 74 that extends radially inward relative to the cylindrical portion of the syringe body 12. In addition, as shown in FIG. 2A, the adapter 18 is formed with a raised distal tab 76 and a raised proximal tab 78 that is formed with a ramp. As shown, the proximal tab 78 is axially spaced from the distal tab 76 to create a gap between the tabs 76, 78. Typically, as shown in FIGS. 3A and 3B, four sets of tabs 76, 78 are uniformly distributed about the circumference of the adapter 18. Functionally, the tabs 76, 78 releasably hold the flange 74 of the syringe body 12 in the gap when the syringe body 12 is in an operational position and releases the flange 74 for proximal movement relative to the adapter 18 into a locking position. In the operational position, as shown in FIG. 2A, the syringe body 12 does not interfere with relative movement between the guard 20 and adapter 18. In the locking position, as shown in FIG. 2E, the flange 74 deflects the cam lever 68 and holds the cam lever 68 in a position where the guard 20 is locked. After an injection, the syringe body 12 can be moved proximally relative to both the plunger 22 and the adapter 18 and into the locking position shown in FIG. 2E. This then locks the guard 20 into position covering the needle tip 28 and prevents inadvertent reuse of the syringe 10.

Figure 7:
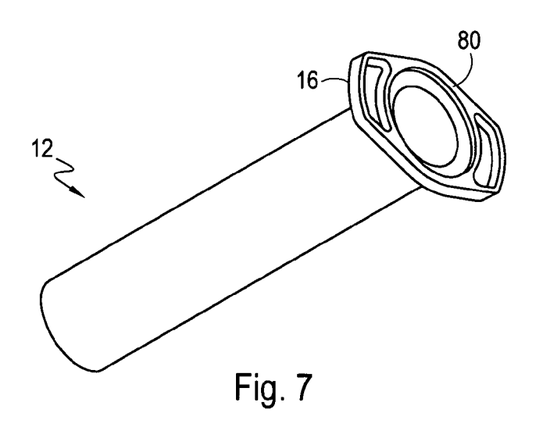
FIG. 7 is a perspective view of a syringe body for use in the syringe shown in FIG. 1.

Cross referencing FIG. 2E with FIG. 7, it can be seen that the finger grip 16 of the syringe body 12 is formed with a recess 80 at the body's proximal end. Specifically, as best seen in FIG. 2E, the recess 80 is sized and positioned to receive the grip flange 24 that is formed at the proximal end 38 of the plunger 22. Functionally, the plunger 22 can be advanced distally after an injection until the grip flange 24 is positioned in the recess 80. With the grip flange 24 positioned in the recess 80, subsequent movement of the plunger 22 relative to the syringe body 12 is effectively prevented.

OPERATION

The syringe 10 is typically delivered to the end user configured as shown in FIG. 2A. Specifically, as FIG. 2A shows, the plunger 22 is initially located in a distal position relative to the adapter 18 with the tang 44 extending into the slot 54 to prevent distal movement of the guard 20. In this configuration, it can be seen that the cylindrical portion 36 of the plunger 22 holds the cam lever 68 deflected inward to lock the guard 20 and prevent proximal movement of the guard 20. As illustrated by FIG. 2B, use of the syringe 10 begins by withdrawing the plunger 22 proximally. FIG. 2B shows this proximal movement of the plunger 22 has several effects. For one, initial proximal movement of the plunger 22 allows the cam lever 68 to relax outwardly from the needle 26 and unlock the guard 20 for proximal movement relative to the needle 26. Additional proximal movement of the plunger 22 engages the tang 44 with the proximal abutment 58, causing the guard 20 to move proximally with the plunger 22. Also, proximal movement of the plunger 22 draws air through the needle 26 and into the medicament chamber 42.

Figure 2C:
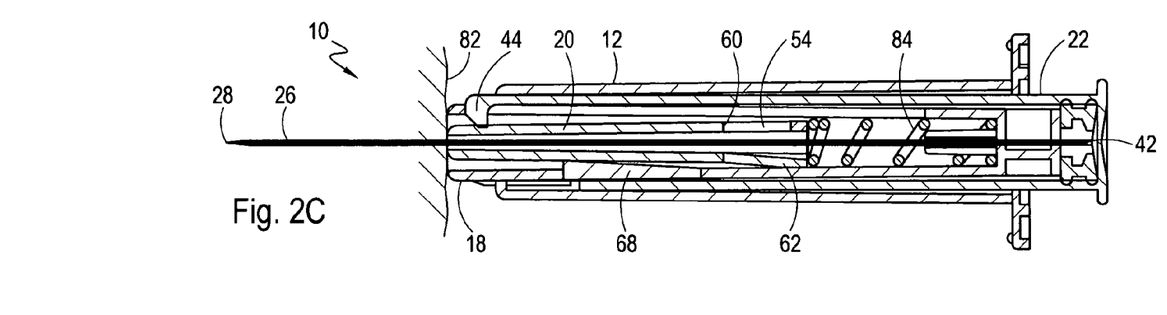
FIG. 2C is a sectional view of the syringe as in FIG. 2A, shown after the needle's distal tip has been inserted into an object (i.e. medicament vial or patient) and thereafter the plunger has been advanced proximally.

Once the guard 20 has been retracted as shown in FIG. 2B, the next step is to insert the exposed distal needle tip 28 into a medicament vial (illustrated by surface 82 in FIG. 2C). At this point, the plunger 22 can be depressed as shown in FIG. 2C to expel air into the vial and void the medicament chamber 42. Comparing FIG. 2B with FIG. 2C, it can be seen that during advancement of the plunger 22, the ramp 60 formed at the distal end of the slot 54 directs the tang 44 out of the slot 54 and disengages the guard 20 from the plunger 22. Thus, as illustrated by FIG. 2C, after depressing the plunger 22, distal movement of the guard 20 is only prevented by the contact between the guard 20 and the surface 82. Next, the plunger 22 can be withdrawn to fill the chamber 42 with medicament (note FIG. 2B is representative of the configuration of the syringe 10 after the chamber 42 is filled with medicament). From FIG. 2B, it can be seen that during withdrawal of the plunger 22, the tang 44 reenters the slot 54 and engages the proximal abutment 58. The result is that the plunger 22 engages the guard 20 and prevents distal advancement of the guard 20 relative to the needle 26. As illustrated by FIG. 2B, when the needle 26 is removed from the vial, the distal tip 28 of the needle 26 remains unguarded and exposed. The syringe 10 is now ready for an injection.

Figure 2D:
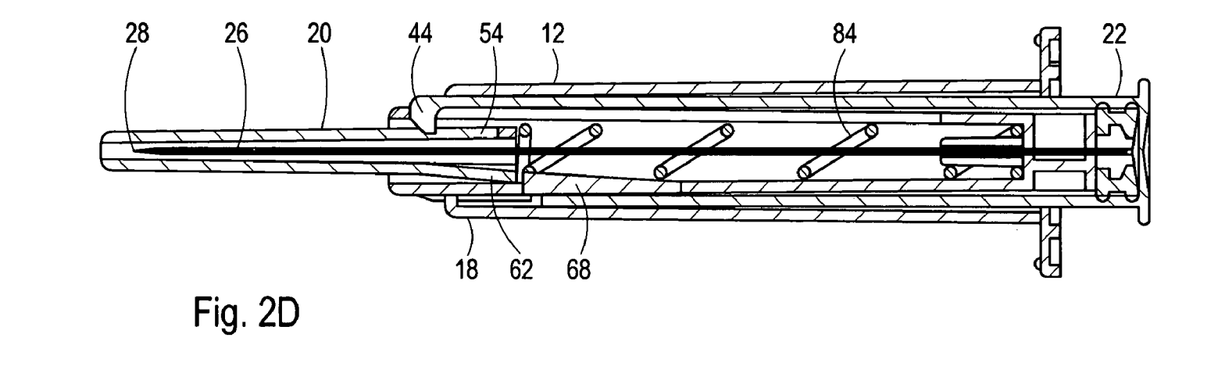
FIG. 2D is a sectional view of the syringe as in FIG. 2A, shown after the needle has been withdrawn from a patient after an injection.
Figure 2E:
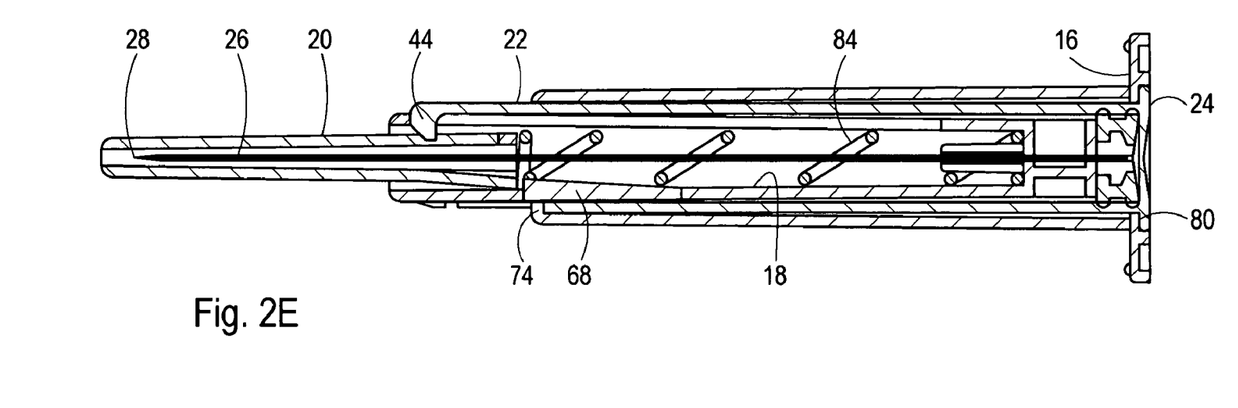
FIG. 2E is a sectional view of the syringe as in FIG. 2A, shown after the plunger and adapter have been advanced distally relative to the syringe body to lock the guard in position and prevent inadvertent reuse of the syringe.

As illustrated by FIG. 2C, to inject a medicament into a patient, the distal tip 28 of the needle 26 is inserted into the patient (represented by surface 82) and the plunger 22 depressed. As shown in FIG. 2C, the distal advancement of the plunger 22 releases the guard 20. Specifically, during advancement of the plunger 22, the ramp 60 directs the tang 44 out of the slot 54 and disengages the guard 20 from the plunger 22. Once released, the guard 20 is free to move distally under the influence of a coil spring 84 that is interposed between the guard 20 and adapter 18. Thus, as the needle 26 is withdrawn from the patient, the needle 26 retracts proximally into the guard 20 which remains in contact with the patient's skin (represented by surface 82). FIG. 2D shows the syringe 10 after the needle 26 has been withdrawn from the patient and the needle 26 has passively retracted into the guard 20. Comparing FIG. 2C with FIG. 2D, it can be seen that the hinge 62 deflects to advance distally past the cam lever 68.

Comparing FIG. 2D with FIG. 2E, it can be seen that once the syringe 10 has been removed from the patient (FIG. 2D), the plunger 22 and adapter 18 can be advanced distally relative to the syringe body 12 to lock the guard 20 in place (FIG. 2E). FIG. 2E also shows that this places the grip flange 24 of the plunger 22 in the recess 80 formed in the syringe body 12. Functionally, once the syringe 10 is in the configuration shown in FIG. 2E, the plunger 22 is disabled and the guard 20 completely covers the hollow needle 26 to protect the user from unwanted needle sticks and prevents inadvertent reuse of the syringe 10.

While the particular devices and methods as herein shown and disclosed in detail are fully capable of obtaining the objects and providing the advantages herein before stated, it is to be understood that they are merely illustrative of the presently preferred embodiments of the invention and that no limitations are intended to the details of construction or design herein shown other than as described in the appended claims.

What is claimed is:

1. A syringe for expelling fluid from a fluid chamber, said syringe comprising:
   an elongated hollow needle defining an axis and having a proximal end, and a distal end formed with a needle tip;
   an adapter for holding the proximal end of the hollow needle with the hollow needle extending in a distal direction from said adapter, said adapter being formed with an axially aligned slit;
   a guard formed with a slot and disposed on said needle for reciprocal axial movement thereon;
   a spring positioned between said guard and said adapter for biasing said guard along said axis in a distal direction from said adapter;
   an inverted plunger, said plunger being hollow and cylindrical shaped and having a closed proximal end and an open distal end; and
   a tang extending distally from said inverted plunger and inwardly through the slit of said adapter toward the needle axis for engagement with the slot of said guard, said plunger being axially moveable relative to said adapter in a proximal direction to create the fluid chamber, and moveable in a distal direction to expel fluid from said fluid chamber as said proximal end of said plunger moves in a distal direction against fluid in said chamber, and wherein during movement in the distal direction said plunger moves from a first (proximal) plunger position wherein said tang of said plunger holds said guard at a retracted location to expose said needle tip and into a second (distal) plunger position wherein said tang of said plunger releases said guard to cover and protect said needle tip.

2. A syringe as recited in claim 1 wherein said syringe further comprises a seal attached to said needle to establish a medicament chamber in said inverted plunger with said medicament chamber in fluid communication with said hollow needle.

3. A syringe as recited in claim 2 wherein said guard is formed with an axially aligned slot having a proximal abutment and said tang of said plunger is extendable into said slot for engagement with said proximal abutment during a proximal movement of said plunger relative to said needle.

4. A syringe as recited in claim 3 wherein said axially aligned slot has a distal ramp to disengage said tang from said guard during a distal movement of said plunger relative to said needle.

5. A syringe as recited in claim 2 wherein said adapter is formed with an axially aligned slit and said tang extends through the slit for extension into the slot in said guard.

6. A syringe as recited in claim 1 wherein said adapter is formed with a cam lever having a distal lever end and a cam surface, said cam lever deflectable from a relaxed position to a biased position with said lever end being closer to said needle in said biased position than said relaxed position, said biased position for engaging said distal lever end with said guard to prevent a retraction of said guard from a needle tip covering position, and wherein said cam surface is positioned for interaction with said plunger to move said cam lever to said biased position during a distal movement of said plunger and return said cam lever to said relaxed position during a proximal movement of said plunger.

7. A syringe as recited in claim 6 further comprising a syringe body formed with a flange and a finger grip, said syringe body being slidingly mounted on said adapter for relative axial movement thereon between an operational position and a locking position wherein said flange engages said cam surface and holds said cam lever in said biased position to lock said guard into a needle tip covering position and prevent reuse of the syringe.

8. A syringe as recited in claim 7 wherein said plunger has a proximal end and is formed with a grip flange at said proximal end and wherein said finger grip of said syringe body is formed with a recess to receive said grip flange after an injection to prevent subsequent movement of said plunger relative to said syringe body.

9. A syringe as recited in claim 7 wherein said adapter is formed with a raised distal tab and a raised proximal tab formed with a ramp, said proximal tab being spaced from said distal tab to create a gap therebetween, said tabs for releasably holding the flange of said syringe body in said gap when said body is in said operational position and releasing said flange for proximal movement relative to said adapter into said locking position.

10. A syringe as recited in claim 1 wherein said guard is substantially cylindrically shaped having a distal end and a proximal end and said proximal end of said guard is formed with a living hinge.

11. A fillable injection syringe comprising:
    an elongated hollow needle formed with a lumen, said needle having a distal needle tip and defining an axis;
    an adapter for holding the hollow needle, said adapter being formed with an axially aligned slit;
    an inverted plunger, said plunger being hollow and cylindrical shaped to form a chamber, said plunger having a closed proximal end and an open distal end and being slidingly mounted on said adapter for retraction in a proximal direction to create the fluid chamber and to establish fluid communication between fluid in said chamber and the lumen of said needle and for advancement in a distal direction to move the proximal end of said plunger against fluid in said chamber to expel the fluid therefrom;
    a tang extending distally from said inverted plunger and inwardly toward the needle axis through the slit of said adapter;
    a guard disposed on said needle for reciprocal axial movement thereon, said guard formed with an axially aligned slot having a proximal abutment for interaction with said tang to axially move said guard during a plunger retraction and expose said needle tip for insertion into a medicament vial and then, in sequence, disengage said guard from said tang of said plunger during a distal movement of said plunger to void said chamber, reengage said guard with said tang of said plunger during a plunger withdrawal to load the chamber with medicament and expose said needle for subsequent insertion into a patient, and release said guard from said tang of said plunger during an advance of the plunger in a relative distal direction and a movement of the adapter in a relative proximal direction to inject medicament into said patient; and
    a spring for translating said released guard along said axis in a distal direction from said adapter to cover and protect said needle tip after an injection.

12. A syringe as recited in claim 11 wherein said axially aligned slot has a distal ramp to disengage said tang from said guard during a distal movement of said plunger relative to said needle.

13. A syringe as recited in claim 11 wherein said adapter is formed with an axially aligned slit and said tang extends through the slit for extension into the slot in said guard.

14. A syringe as recited in claim 11 wherein said adapter is formed with a cam lever having a distal lever end and a cam surface, said cam lever moveable between a relaxed position and a biased position with said lever end being closer to said needle in said biased position than said relaxed position, said biased position for engaging said distal lever end with said guard to prevent a retraction of said guard from a needle tip covering position, and wherein said cam surface is positioned for interaction with said plunger to move said cam lever to said biased position during a distal movement of said plunger and return said cam lever to said relaxed position during a distal movement of said plunger.

15. A syringe as recited in claim 14 further comprising a syringe body formed with a flange and a finger grip, said syringe body being slidingly mounted on said adapter for relative axial movement thereon between an operational position and a locking position wherein said flange engages said cam surface and holds said cam lever in said biased position and locks said guard into a needle tip covering position to prevent reuse of the syringe.

16. A syringe as recited in claim 15 wherein said plunger has a proximal end and is formed with a grip flange at said proximal end and wherein said finger grip is formed with a recess to receive said grip flange after an injection to prevent subsequent movement of said plunger relative to said syringe body.

17. A syringe as recited in claim 16 wherein said adapter is formed with a raised distal tab and a raised proximal tab formed with a ramp, said proximal tab being axially spaced from said distal tab to create a gap therebetween, said tabs for releasably holding the flange of said syringe body in said gap when said body is in said operational position and releasing said flange for proximal movement relative to said adapter into said locking position.

18. A method for injecting a medicament into a patient and passively protecting the used syringe thereafter, said method comprising the steps of:
   providing a syringe having a hollow needle formed with a tip and defining an axis, an adapter for holding the needle, an inverted plunger, said plunger being hollow and cylindrical shaped to form a chamber having a tang extending distally from said inverted plunger and inwardly through a slit in the adapter toward the needle axis, said plunger having a closed proximal end and an open distal end and being slidingly mounted on said adapter for retraction in a proximal direction to create the fluid chamber, a guard disposed on said needle for reciprocal axial movement thereon, said guard formed with an axially aligned slot having a proximal abutment for interaction with said tang when said plunger is withdrawn in a proximal direction, and a spring positioned to bias said guard and adapter in opposite axial directions;
   retracting said plunger to engage said tang thereof with said guard to axially move said guard and expose said needle tip;
   inserting said tip into a medicament vial;
   advancing said plunger in a distal direction to disengage said guard from said tang of said plunger and void said chamber;
   withdrawing said plunger to reengage said guard with said tang of said plunger and load the chamber with medicament;
   inserting the tip of said needle into a patient;
   depressing said plunger to move the proximal end of said plunger in a distal direction against medicament in the chamber to inject the medicament from the chamber through the needle and into the patient and to release said guard from said tang of said plunger; and
   removing said needle tip from the patient to slide said guard distally relative to said needle to cover and protect said needle tip.

19. A method as recited in claim 18 wherein said syringe further comprises a syringe body slidingly mounted on said adapter for relative axial movement thereon and said method further comprises the step of moving said plunger and adapter relative to said syringe body to lock said guard into a needle tip covering position and prevent reuse of the syringe.

20. A method as recited in claim 18 wherein said adapter is formed with an axially aligned slit and said tang extends through the slit for extension into the slot in said guard.

* * * * *